US011278441B2

(12) United States Patent
Saban

(10) Patent No.: US 11,278,441 B2
(45) Date of Patent: Mar. 22, 2022

(54) MODULAR SUPPORTIVE SPINAL BRACE

(71) Applicant: Clint Saban, Woolgoolga (AU)

(72) Inventor: Clint Saban, Woolgoolga (AU)

( * ) Notice: Subject to any disclaimer, the term of this patent is extended or adjusted under 35 U.S.C. 154(b) by 391 days.

(21) Appl. No.: 16/489,951

(22) PCT Filed: Feb. 22, 2018

(86) PCT No.: PCT/AU2018/050143
§ 371 (c)(1),
(2) Date: Aug. 29, 2019

(87) PCT Pub. No.: WO2018/157196
PCT Pub. Date: Sep. 7, 2018

(65) Prior Publication Data
US 2020/0000621 A1    Jan. 2, 2020

(30) Foreign Application Priority Data

Mar. 3, 2017    (AU) ................................ 2017900728

(51) Int. Cl.
*A61F 5/02*    (2006.01)
*A61F 5/058*    (2006.01)

(52) U.S. Cl.
CPC .......... *A61F 5/026* (2013.01); *A61F 5/05883* (2013.01)

(58) Field of Classification Search
CPC ........ A61F 5/026; A61F 5/05883; A61F 5/03; A61F 5/058; A61F 5/02; A61F 5/37; A61F 5/05808; A61F 5/01; A61F 5/00; A61F 5/05833; A61F 5/05816; A61F 5/055; A61F 5/24; A61F 5/30; A61F 5/028; A41C 3/00
See application file for complete search history.

(56) References Cited

U.S. PATENT DOCUMENTS

| 7,316,660 B1 | 1/2008 | Modglin |
| 8,216,167 B2 | 7/2012 | Garth et al. |
| 2010/0262054 A1 | 10/2010 | Summit et al. |

(Continued)

FOREIGN PATENT DOCUMENTS

| DE | 10359105 A1 * | 1/2005 | ............... A61F 5/02 |
| DE | 10359105 A1 | 1/2005 | |

(Continued)

OTHER PUBLICATIONS

International Search Report dated Jun. 4, 2018 from corresponding PCT Application No. PCT/AU2018/050143.

*Primary Examiner* — Tarla R Patel
(74) *Attorney, Agent, or Firm* — Innovation Capital Law Group, LLP; Vic Lin

(57) ABSTRACT

A supportive spinal brace easily configurable to support disabled or injured and various chosen postures. The spinal brace comprises a plurality of rotatably interlocking components (101). The rotatably interlocking components are able to interlock together line at various user configurable rotational offsets to form a user configurable supportive undulation along the length of the brace. In an embodiment, the rotatably interlocking components define portions which interlock together at medial side (104, 105) thereof and at lateral sides (106) thereof with laterally adjacent plates (108), thereby supporting each interlocking portion at both medial and lateral sides thereof for enhanced structural integrity of the brace.

21 Claims, 9 Drawing Sheets

(56) References Cited

U.S. PATENT DOCUMENTS

2015/0094633 A1    4/2015   Garcia
2015/0297387 A1   10/2015  Thompson et al.

FOREIGN PATENT DOCUMENTS

| DE | 102012017645 | | 8/2013 | |
| DE | 102012017645 | B3 * | 8/2013 | ............... A61F 5/02 |
| EP | 1854435 | A2 * | 11/2007 | ............. A61F 5/024 |
| EP | 1854435 | A2 | 11/2007 | |
| TW | 201106934 | A | 3/2011 | |

* cited by examiner

MODULAR SUPPORTIVE SPINAL BRACE

FIELD OF THE INVENTION

This invention relates generally to a modular supportive spinal brace for the injured or disabled.

BACKGROUND OF THE INVENTION

A need exists for a configurable spinal supportive brace for people being immobile on account of physical disability or injury.

The brace should be adjustable so as to support the spine in various positions. Furthermore, the brace should be attachable to various mobility items. Also, the brace should be sufficiently robust.

US 2010/0262054 A1 (SUMMIT et al.) 14 Oct. 2010 [hereinafter referred to as D1] discloses a way to fabricating a custom brace which includes marking a body with reference points and/or other indicators. Multiple images of the body from multiple angles are then obtained. The images are used to determine the contours of the body and the other markings are located and used to design the custom brace. Fenestrations can be added to the brace design. The custom brace can be fabricated with the fenestrations as a single piece structure or in multiple pieces that are assembled to complete the custom device.

U.S. Pat. No. 7,316,660 B1 (MODGLIN) 8 Jan. 2008 [hereinafter referred to as D2] discloses a spinal orthosis for treating a spine, including an anterior support and a posterior support, each support made of a laminate having a flexible foam material and a substantially rigid plastic sheet material sandwiched between a pair of soft flexible sheet materials and bonded together to yield a unitary and substantially rigid laminate material.

The present invention seeks to provide a non-medicated supportive spinal brace, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein a supportive spinal brace easily configurable to support disabled or injured and various chosen postures.

Specifically, the spinal brace comprises a plurality of rotatably interlocking components. The rotatably interlocking components are able to interlock together in-line at various user configurable rotational offsets to form a user configurable supportive undulation along the length of the brace.

Furthermore, in a preferred embodiment, the rotatably interlocking components define portions which interlock together at medial side thereof and at lateral sides thereof with laterally adjacent plates, thereby supporting each interlocking portion at both medial and lateral sides thereof for enhanced structural integrity of the brace.

In embodiments, the brace further comprises elongate plate connectors that further extend between adjacent laterally adjacent plates of the brace, thereby further enhancing the structural rigidity of the brace.

In one embodiment, the components interlock together by way of corresponding male and female meshing having elongate bolts inserted widthwise therethrough. The meshing allows the rotational offset at increments, such as at 15° increments. In one embodiments, each adjacent rotatably interlocking component can be offset between +30° and −30° with respect to an adjacent rotatably interlocking component.

As such, with the foregoing in mind, in accordance with one aspect, there is provided a supportive spinal brace comprising: a plurality of rotatably interlocking components, each defining: a superior rotatable interlock portion defining a medially facing interlock; and an inferior rotatable interlock portion defining an oppositely located and oppositely handed medially facing interlock and wherein: respective medially facing interlocks of adjacent interlocking components are able to interlock together at user configurable rotational offsets to form a user configurable undulating supportive surface long a length of the brace.

The rotatable interlock portions may each further define a laterally facing interlock and wherein the brace may further comprise a plurality of lateral interlock components having a lateral plate, the lateral plate having a pair of medially facing interlocks which interlock between laterally facing interlocks of adjacent interlocking components.

Each interlock portion may comprise a convex cylindrical end profile having a radius and an opposite concave cylindrical end profile of the same radius for rotational articulation between corresponding convex and concave cylindrical end profiles of adjacent rotatably interlocking components.

The concave cylindrical end spans an arc less than 180°.

The convex cylindrical end profile may spans an arc greater than 180°.

The convex and concave cylindrical end profiles may be configured for between approximately +30° to −30° adjustment between adjacent rotatably interlocking components.

The lateral interlock components may each define a bearing plate orthogonal to the lateral plate.

The brace may further comprise 90° bracing between the bearing plate in the lateral plate.

The bearing plate may extend both medially and laterally with respect to the lateral plate.

The rotatable interlock portions and the lateral interlock components may define coaxial bolt through holes through the respective interlocks for widthwise insertion of bolts therethrough.

The brace may further comprise a plurality of elongate plate connectors each having opposite sockets for the bolts and wherein each plate connector may be configured for spanning between adjacent interlocks of adjacent lateral interlock components.

Each plate connector may define a pair of medially facing interlocks and wherein each lateral plate defines a pair of corresponding laterally facing interlocks.

The medially facing interlock of the superior rotatable interlock portion may comprise male meshing and wherein the medially facing interlock of the inferior rotatable interlock portion may comprise corresponding female meshing.

The meshing may comprise teeth offset at approximately 15° offset increments.

The laterally facing interlock of the rotatable interlock portions may comprise female meshing and wherein the medially facing interlocks of the lateral plates comprise corresponding male meshing.

The laterally facing interlocks of the lateral plates may define female meshing and wherein the medially facing interlocks of the elongate plate connectors comprise corresponding male meshing.

A subset of the rotatably interlocking components may comprise a posterior tubular section for insertion of a tube of tubular bracework therethrough.

The brace may further comprise the tubular brace work and wherein the tubular brace work may comprise at least one of a tubular T-Piece, 90° and parallel offset components.

Distal ends of the components may comprise apertures for the insertion of a through pin of a circlip connected therethrough.

The brace may further comprise a head support component comprising a right angled bracket supporting a curved portion.

The head support component may be attachable to an anterior surface of an adjacent bearing plate.

The head support component may be widthwise adjustably attachable to the anterior surface of the adjacent bearing plate.

Medial faces of the lateral plates may define a vertical channel and wherein anterior surface of the rotatably interlocking components define a widthwise channel.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
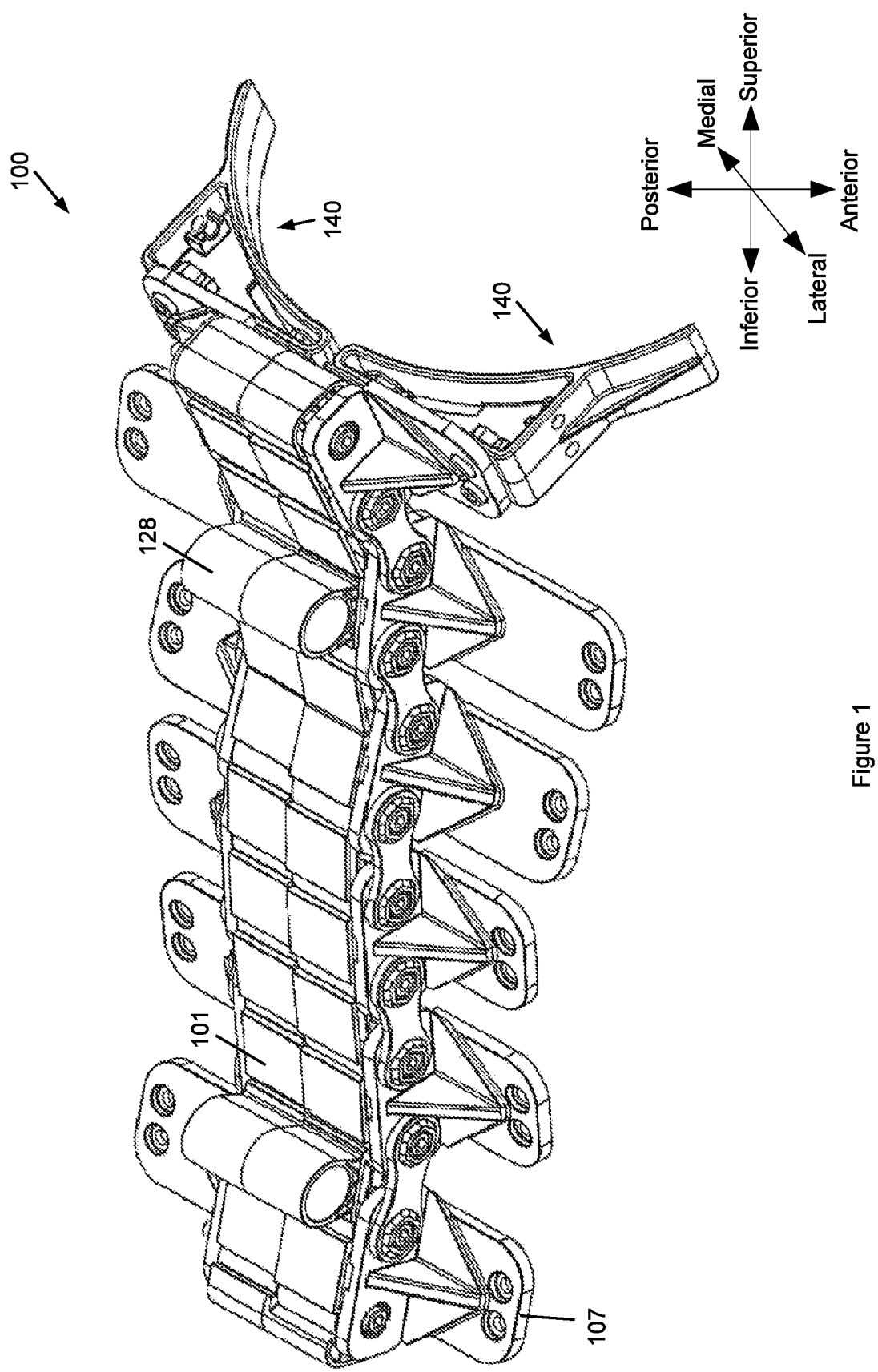
FIG. 1 shows a posterior perspective view of an assembled supportive spinal brace in accordance with an embodiment.
Figure 2:
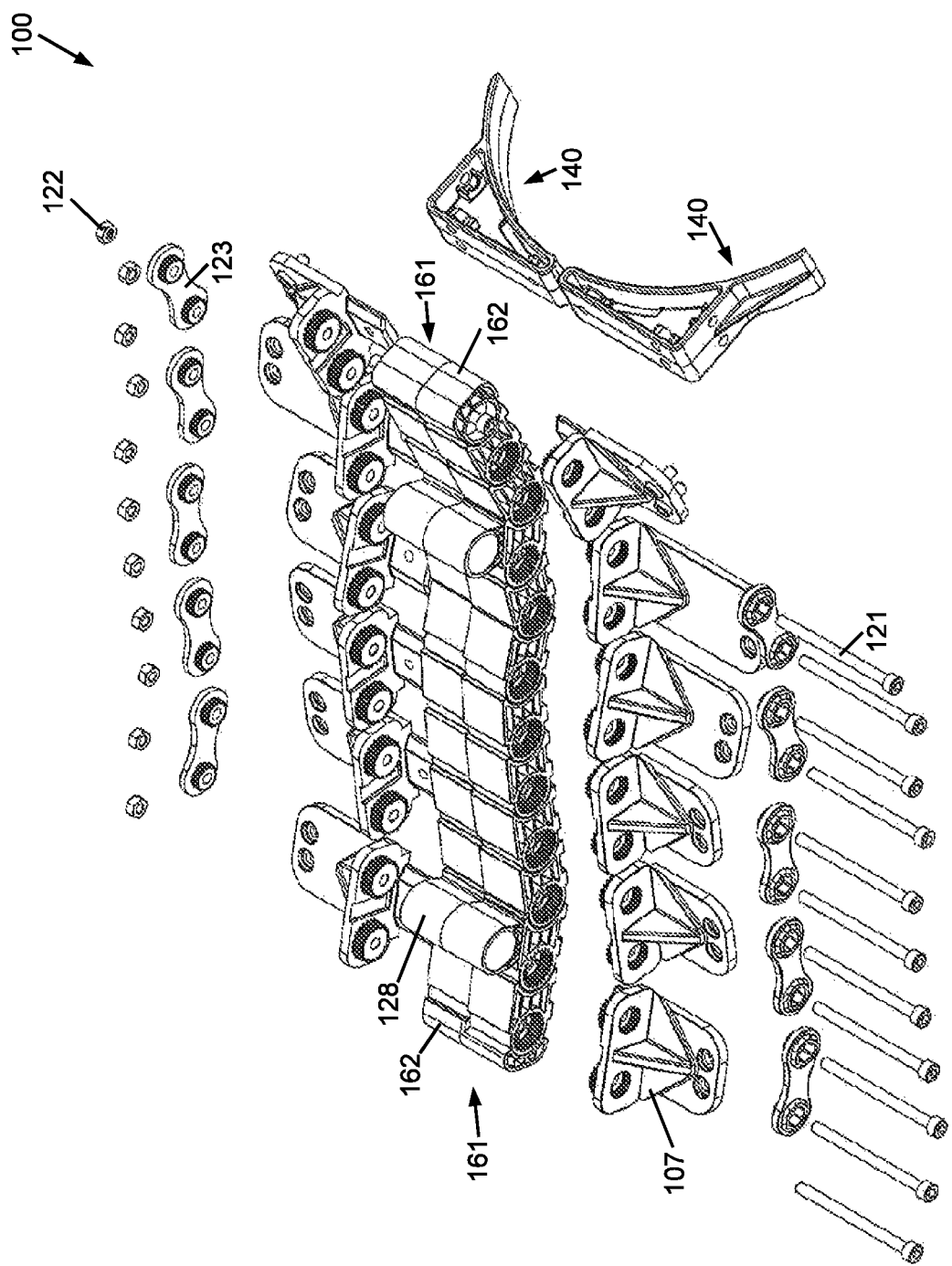
FIG. 2 shows a corresponding exploded representation of the brace of FIG. 1 in accordance with an embodiment.

FIG. 1 shows an underside view of a constructed modular supportive spinal brace 100 whereas FIG. 2 shows a corresponding exploded representation thereof.

In an embodiment, the brace 100 may be manufactured from plastic material. Further, as will be appreciated from the ensuing description, the various componentry described herein are configured so as to be suited for injection molding.

For orientational convenience, reference will be made to the orientational axes provided in FIG. 1 wherein the brace 100 is described as running lengthwise from the superior/head end to the inferior/tail end, having anterior/upper and posterior/under surfaces and having outer/lateral sides and medial/middle portions.

Figure 4:
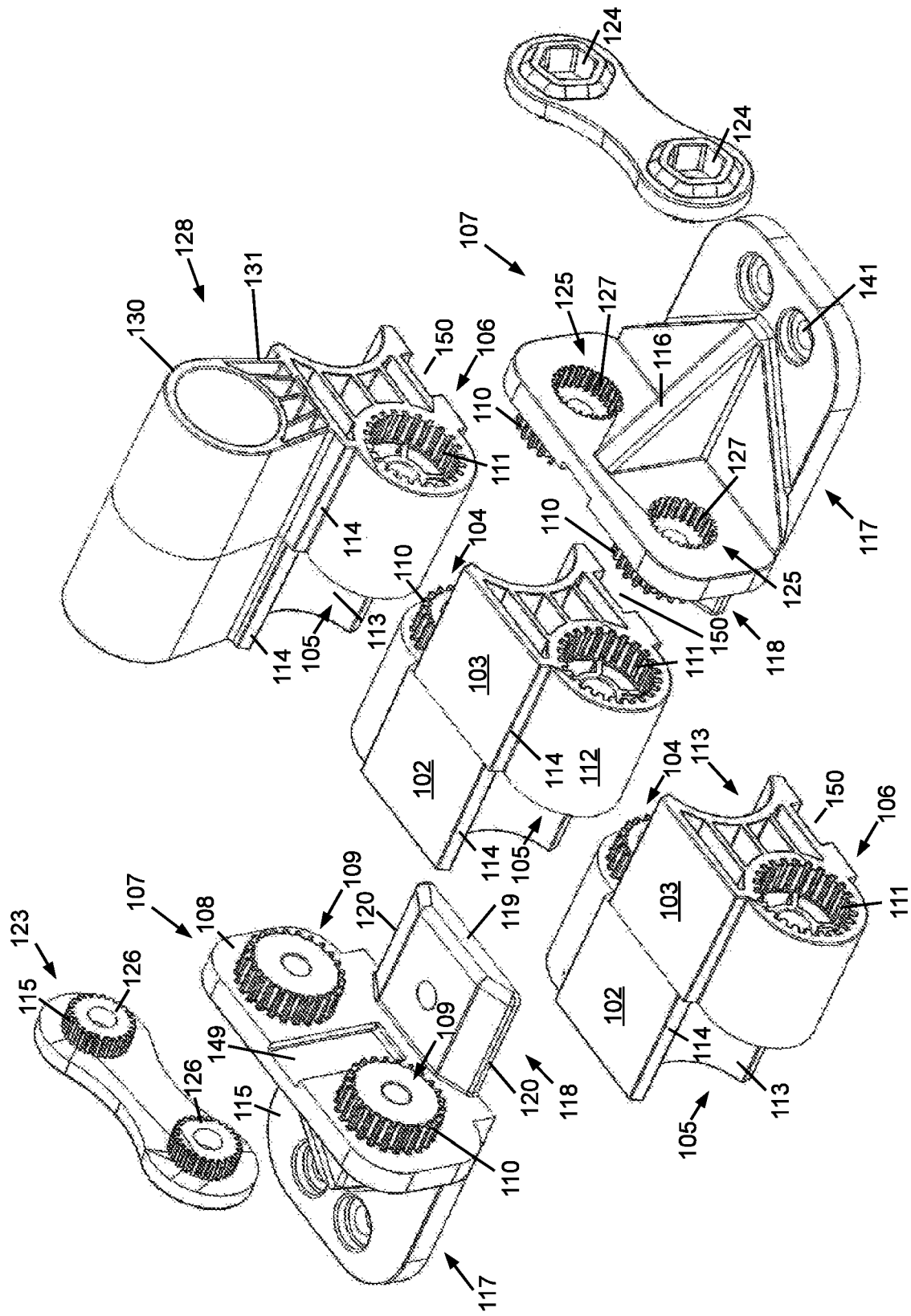
FIG. 4 shows a posterior exploded representation of constituent components of the brace in accordance with an embodiment.

FIG. 4 illustrates the spinal brace 100 comprising a plurality of rotatably interlocking components 101. Each rotatably interlocking component 101 comprises a superior rotatable interlock portion 102 and an inferior rotatable interlock portion 103, which may be integrally formed. The superior rotatable interlock portion 102 defines a medially facing interlock 104 and the inferior rotatable interlock portion 103 defines an oppositely located and oppositely handed medially facing interlock 105.

The respective medial facing interlocks 104, 105 of adjacent rotatably interlocking components 101 are able to interlock together in line at user configurable rotational offsets to form a user configurable supportive undulation along the length of the brace 100.

In the embodiment shown in FIG. 4, the rotatable interlock portions 102, 103 each further define laterally facing interlocks 106. In this regard, the brace 100 may further comprise a plurality of lateral interlock portions 107 each having a lateral plate 108. Each lateral plate 108 defines a pair of medially facing interlocks 109 which interlock in-line at user configurable rotational offsets between respective laterally facing interlocks 106 of adjacent pairs of interlocking components 101. In this way, each rotatable interlock portion 102, 103 can interlock both at medial and lateral faces, thereby enhancing the structural rigidity of the brace 100.

In the embodiment shown in FIG. 4, the interlocks 104, 105, 109 may comprise male and female meshing. Specifically, the medially facing interlock 104 of the superior rotatable interlock portion 102 defines male meshing 110 which slides into a corresponding female meshing of the medially facing interlock 105 of the inferior rotatable interlock portion 103.

Correspondingly, the medially facing interlocks 109 of the lateral plate 108 comprises male meshing 110 which slides into corresponding female meshing 111 of the respective laterally facing interlocks 106 of the rotatable interlock portions 102, 103.

In embodiments, teeth of the meshing are offset at 15° so as to allow for user configurable rotational offset by 15° increments.

In the embodiment shown, each interlock portion 102, 103 comprises a convex cylindrical end profile 112 having a radius and an opposite concave cylindrical end profile 113 of the same radius. As such, the convex cylindrical profile 112 is able to rotatably articulate within the corresponding concave cylindrical end profile 113.

In the embodiment shown, the convex cylindrical end profile 112 spans through an arc of greater than 180° and the concave cylindrical end profile 113 correspondingly span through an arc of less than 180° such that the terminating edges 114 thereof allow posterior/anterior rotational tolerance.

In embodiments, the posterior/anterior rotational tolerance is between +30° and −30°.

The lateral interlock portions 107 may further comprise a bearing plate 115 being orthogonal with respect to the lateral plate 108. The bearing plates 115 define an anterior spine supporting surface. 90° bracing 116 may span between the lateral plate 109 and the bearing plate 115 for reinforcement.

In the embodiment shown, the bearing plate 115 extends both laterally and medially with respect to the lateral plate 108.

Specifically, as can be seen, the bearing plate 115 defines a lateral portion 117 which extends laterally with respect to the lateral plate 108 and a medial portion 118 which extends medially with respect to the lateral plate 108.

In embodiments, lateral portions 117 of differing spans may be provided such as illustrated in FIGS. 1 and 2 wherein the inferior lateral portions 117 are shorter than those of the superior lateral portions 117 such that the brace 100 widens from the coccyx to the wider upper back of the user.

In embodiments, the medial faces 119 of the medial portions 118 may leave a gap of approximately 7 mm between a respective opposite medial face 118 of the opposite medial portion 118. Furthermore, the medial portions 118 may comprise a superior/inferior width such that the superior/inferior edges 120 thereof leave a gap to the adjacent superior/inferior edge 120 of an adjacent medial portion 118. Furthermore, the superior/inferior edges 120 may comprise posterior bevelling.

The spacing tolerance around the superior/inferior edges 120 and the medial edges 119 of the medial portions 118 allow for the engagement of padding therearound.

The rotatably interlocking components 101 and the lateral interlock components 107 may be held together by long through bolts 121 and nuts 122 as is substantially shown in FIG. 2. In the embodiment shown, the bolt 121 may comprise an Allen key head.

With reference to FIG. 4, the brace 100 may further comprise a plurality of elongate plate connectors 123 having opposite nuts sockets 124 for non-rotatably engaging a nut 122 inserted laterally therein. As such, for assembly, a nut 122 may be placed within the socket 124 and the distal end of the bolt 121 inserted therethrough from the medial side. Thereafter, using an Allen key, and no other tool, the user is able to screw the bolt 121 into the nuts 122 non-rotatably engaged within the socket 124.

In accordance with this embodiment, the lateral surfaces of the bearing plate 108 may further comprise a plurality of laterally facing interlocks 125 and wherein the elongate plate connectors 123 define a pair of corresponding medially facing interlocks 126 which rotatably engaged at user configurable rotational offsets within the corresponding laterally facing interlocks 125. In this way, each elongate plate connector 123 is configured for spanning between adjacent laterally facing interlocks 125 of adjacent lateral plates 108.

In the embodiment shown, the medially facing interlocks 126 of the plate connectors 123 comprises a male mesh 127 and the laterally facing interlocks 125 of the lateral plates 108 comprises a female mesh 127 of smaller diameter than the corresponding male mesh 110 and female mesh 111 of the rotatable interlock portions 101 and the lateral interlock portions 107 whilst yet comprising the same rotational offset increments of 15°.

Figure 3:
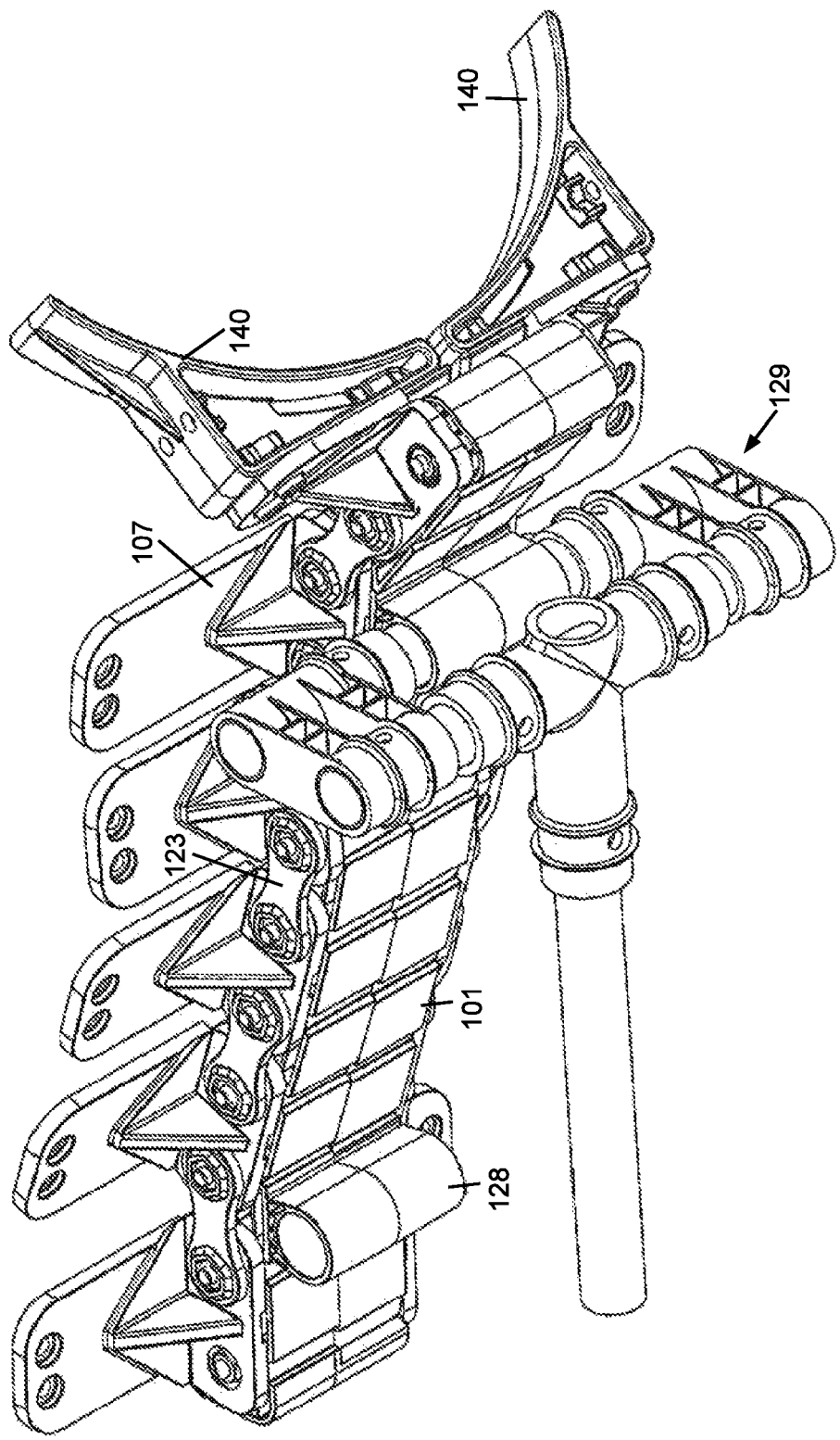
FIG. 3 illustrates the connection of the brace to tubular brace work in accordance with an embodiment.

Certain of the rotatably interlocking components 101 may comprise an attachable or integrally formed tube connector portion 128 extending posteriorly for attachment to tubular bracework 129 as is substantially shown in FIG. 3. In this regard, the tube connector portion 128 may comprise a cylinder 130 supported from strutting 131 for the insertion of tube sections of the tubular brace work 129 therethrough.

FIGS. 9-12 show components of the modular brace work 129 in embodiments. Specifically, with reference to FIG. 9, the tubular brace work 129 may comprise a T-piece connector 132, a right angle connector 133, a terminal connector 134 and a parallel offset connector 135 which may be used in a variety of combinations to assemble tubular brace work 129 of various shapes and/or configuration. The tubular components 132-135 may be connected together using a circlip 136 and throughpin 137 as is substantially shown in FIG. 12. Specifically, distal ends of the components 132, 135 may comprise peripheral flanges 138 defining a collar having a central aperture 139 therein. The collar engages the circlip 136 and the aperture 139 receives the throughpin 137 there through so as to lock the component 132-135 to the tubular piece extending therefrom.

Figure 11:
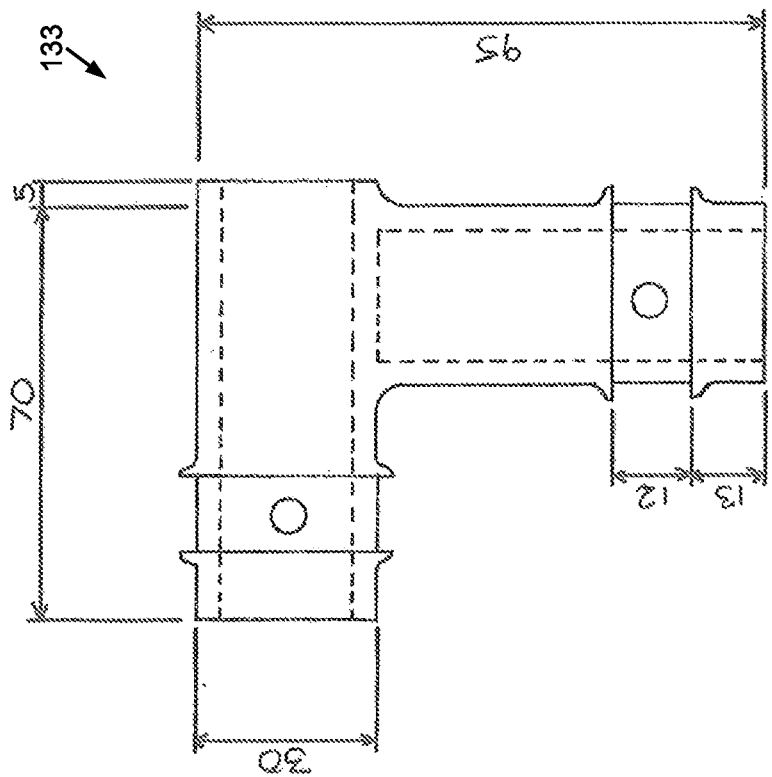
FIGS. 10 and 11 illustrate exemplary dimensions of the componentry of the tubular brace work in accordance with an embodiment.
Figure 10:
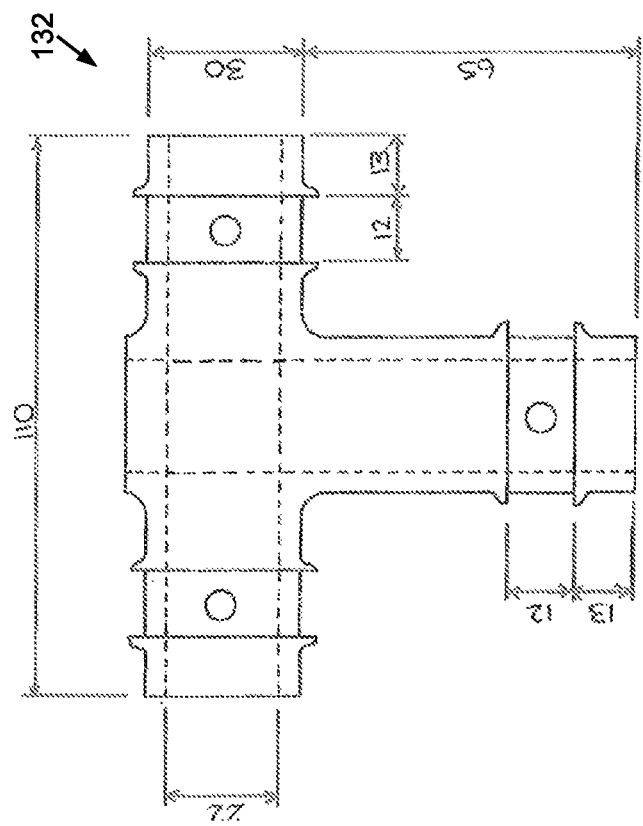
Figure 12:
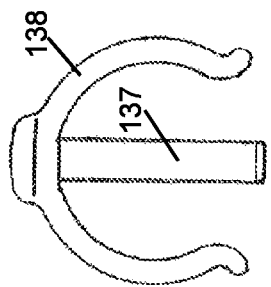
FIG. 12 illustrates a circlip and through pin for attachment of the componentry of the tubular brace work in accordance with an embodiment.

Exemplary dimensions of the T-piece connector 132 and the right angle connector 133 are given respectively in FIGS. 10 and 11.

Figure 6:
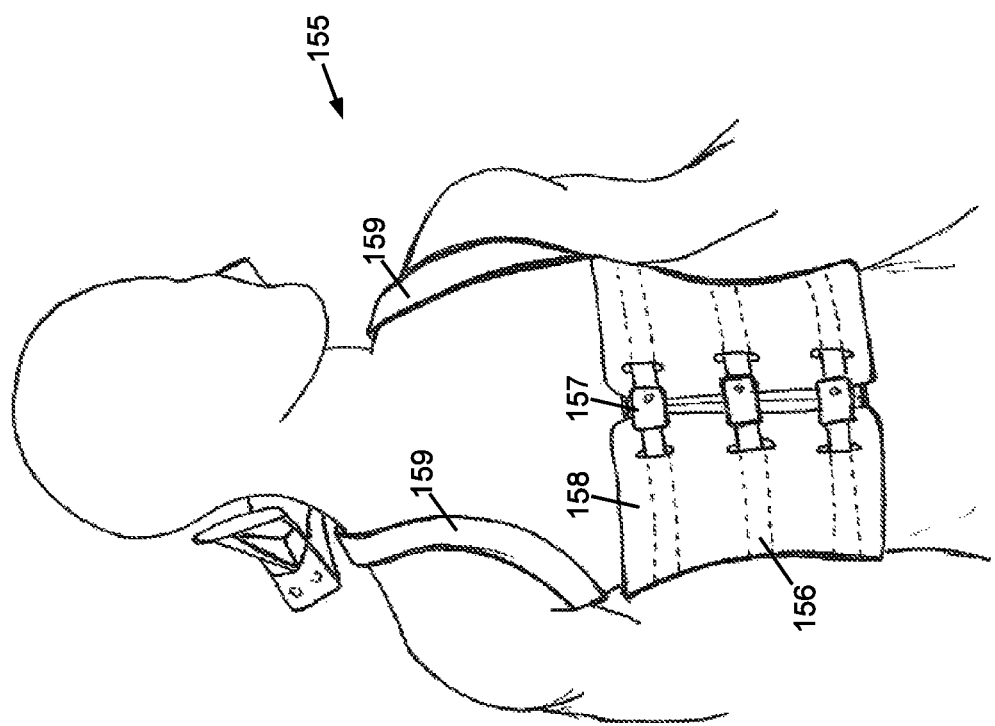
FIGS. 5 and 6 illustrate the utilisation of a harness system for holding the user to the brace in accordance with an embodiment.
Figure 5:
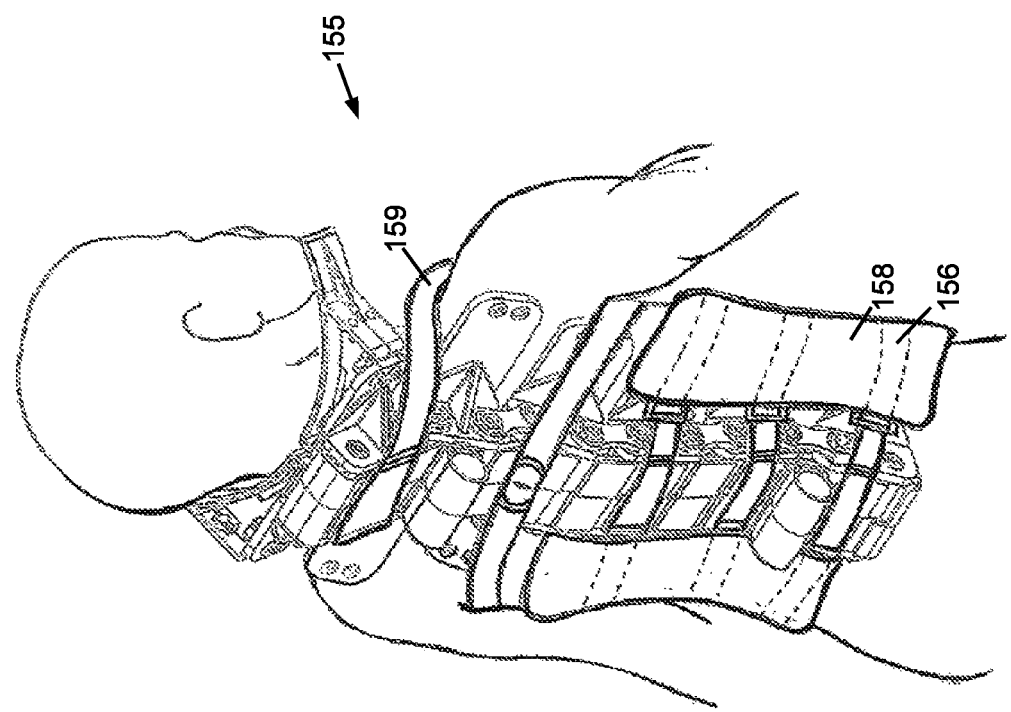
Figure 7:
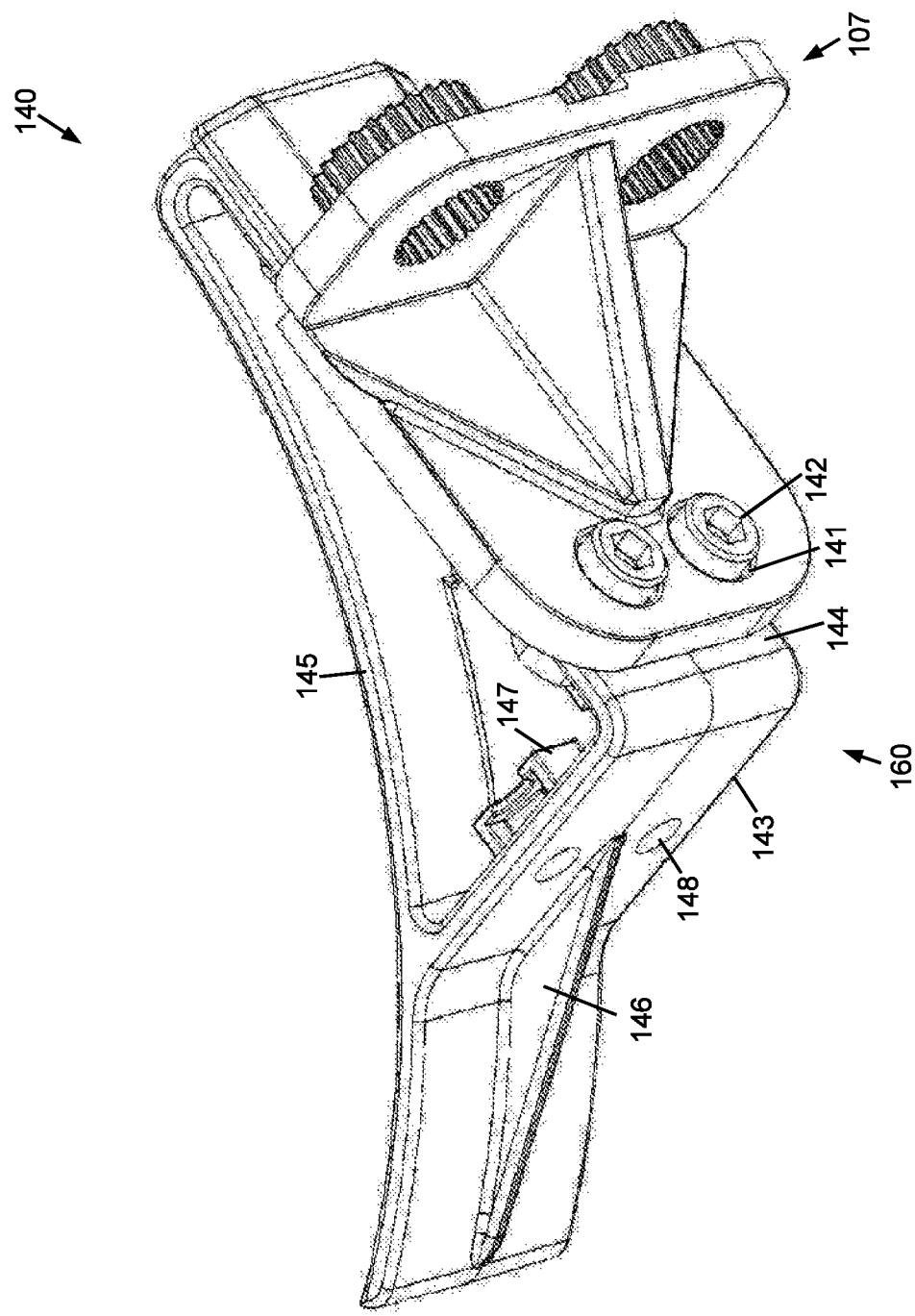
FIG. 7 illustrates a head support component in accordance with an embodiment.

FIG. 7 shows a head support component 140 connectable to a lateral interlock component 107 for supporting the head of the user in the manner substantially given in FIGS. 5 and 6. Specifically, the bearing plates 115 of the lateral interlock components 107 may comprise bolthole apertures 141 through which corresponding short bolts 142 may be inserted. Bolthole apertures of the head support component 140 may be elongate for lateral offset adjustment.

In a preferred embodiment, the short bolts 142 and the long bolts 121 are of M6 sizing.

The head support component 140 comprises a right angled bracket 160 comprising a vertical member 143 and an orthogonal horizontal member 144. The horizontal member 144 has a posterior planar face 144 which lies flush against the corresponding anterior planar face of the bearing plate 115.

The right angled bracket 160 supports a curved portion 145 which ergonomically holds the head and/or neck of the user. Padding may cover the curved portion 145. The curved portion 145 may extend laterally beyond the vertical member 143 and may therefore comprise supportive bracing 146 therefor.

In embodiments, the vertical member 143 may comprise attachment brackets 147 and associated apertures 148 for the attachment of various peripheral componentry such as switch controls, additional head support devices/components or the like.

Figure 8:
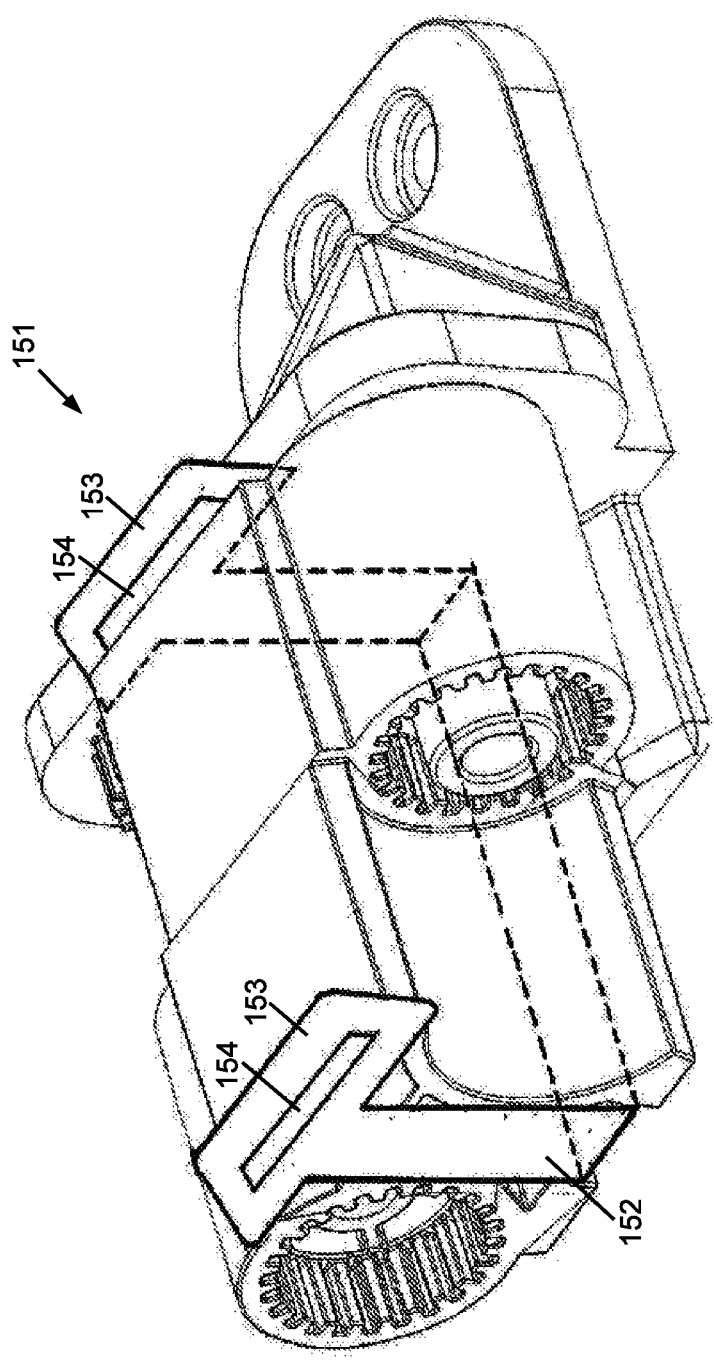
FIG. 8 illustrates the rotatably interlocking components defining a U channel therearound for the engagement of a U-clip therein for attachment in accordance with an embodiment.
Figure 9:
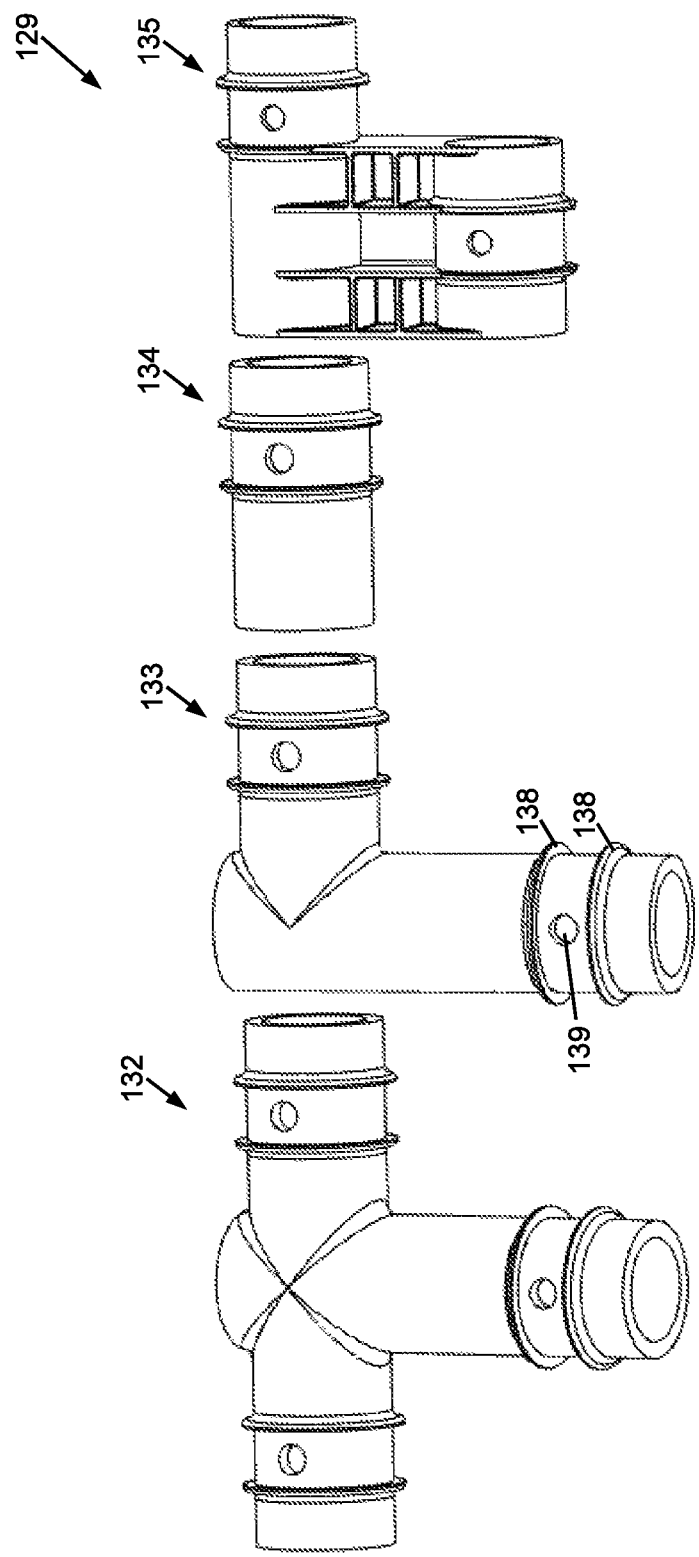
FIG. 9 illustrates various componentry of the tubular brace work in accordance with an embodiment.

With reference to FIG. 4, the medial face of the lateral plate 108 may comprise a vertical channel 149 and the anterior surface of the rotatably interlocking component 101 may comprise a corresponding widthwise channel 150 thereby defining a U-channel for holding a corresponding U-clip 151 as a substantially shown in FIG. 8. Specifically, the U-clip 151 comprises a band 152 which conforms to the so formed U-channel and comprises distal ends 153 comprising elongate strap apertures 154 therethrough. In this way, strapping may be engaged within the respective apertures 154 to secure the brace 100 using strapping.

FIGS. 5 and 6 illustrates an exemplary harness system 155 for holding the user to the brace 100. In accordance with this embodiment, the harness system 155 comprises widthwise strapping 156 and corresponding releasable clips 157 which secure around the trunk of the user. A padded jacket 158 may interface between the strapping 156 and the user for comfort.

Furthermore, shoulder strapping 159 may transition from underarm to behind the neck of the user in the manner shown.

In the embodiment shown in FIG. 2, terminating blanks 161 having rounded ends may be used to terminate a row of rotatably interlocking components 101. Each terminating blank 161 comprises a single rotatable interlock portion 102, 103 for engaging the free corresponding interlock portion 102, 103 of the penultimate rotatably interlocking component 101.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A supportive spinal brace comprising:
 a plurality of rotatably interlocking components (101), each defining:
  a superior rotatable interlock portion (102) defining a medially facing interlock (104); and
  an inferior rotatable interlock portion (103) defining an oppositely located and oppositely handed medially facing interlock (105) and wherein:
 respective medially facing interlocks of adjacent interlocking components are able to interlock together at user configurable rotational offsets to form a user configurable undulating supportive surface long a length of the brace, wherein
 the superior and inferior rotatable interlock portions each further define a laterally facing interlock (106) and wherein the brace further comprises a plurality of lateral interlock components (107) having a lateral plate, the lateral plate (108) having a pair of medially facing interlocks (109) which interlock between laterally facing interlocks of adjacent interlocking components; and
 each of the superior and inferior rotatable interlock portions comprises a convex cylindrical end profile (112) having a radius and an opposite concave cylindrical end profile (113) of the same radius for rotational articulation between corresponding convex and concave cylindrical end profiles of adjacent rotatably interlocking components.

2. The supportive spinal brace as claimed in claim 1, wherein the concave cylindrical end spans an arc less than 180°.

3. The supportive spinal brace as claimed in claim 1, wherein the convex cylindrical end profile spans an arc greater than 180°.

4. The supportive spinal brace as claimed in claim 1, wherein the convex and concave cylindrical end profiles are configured for between approximately +30° to −30° adjustment between adjacent rotatably interlocking components.

5. The supportive spinal brace as claimed in claim 1, wherein the lateral interlock components each define a bearing plate orthogonal to the lateral plate.

6. The supportive spinal brace as claimed in claim 5, further comprising 90° bracing between the bearing plate in the lateral plate.

7. The supportive spinal brace as claimed in claim 5, wherein the bearing plate extends both medially and laterally with respect to the lateral plate.

8. The supportive spinal brace as claimed in claim 5, further comprising a head support component comprising a right angled bracket supporting a curved portion.

9. The supportive spinal brace as claimed in claim 8, wherein the head support component is attachable to an anterior surface of an adjacent bearing plate.

10. The supportive spinal brace as claimed in claim 9, wherein the head support component is widthwise adjustably attachable to the anterior surface of the adjacent bearing plate.

11. The supportive spinal brace as claimed in claim 1, wherein each of the superior and inferior rotatable interlock portions and the lateral interlock components define coaxial bolt through holes through the respective interlocks for widthwise insertion of bolts therethrough.

12. The supportive spinal brace as claimed in claim 11, further comprising a plurality of elongate plate connectors each having opposite sockets for the bolts and wherein each plate connector is configured for spanning between adjacent interlocks of adjacent lateral interlock components.

13. The supportive spinal brace as claimed in claim 12, wherein each plate connector defines a pair of medially facing interlocks and wherein each lateral plate defines a pair of corresponding laterally facing interlocks.

14. The supportive spinal brace as claimed in claim 12, wherein the laterally facing interlocks of the lateral plates define female meshing and wherein the medially facing interlocks of the elongate plate connectors comprise corresponding male meshing.

15. The supportive spinal brace as claimed in claim 1, wherein the laterally facing interlock of each of the superior and inferior rotatable interlock portions comprises female meshing and wherein the medially facing interlocks of the lateral plates comprise corresponding male meshing.

16. The supportive spinal brace as claimed in claim 1, wherein the medially facing interlock of the superior rotatable interlock portion comprises male meshing and wherein the medially facing interlock of the inferior rotatable interlock portion comprises corresponding female meshing.

17. The supportive spinal brace as claimed in claim 16, wherein the meshing comprises teeth offset at approximately 15° offset increments.

18. The supportive spinal brace as claimed in claim 1, wherein a subset of the rotatably interlocking components comprises a posterior tubular section for insertion of a tube of tubular bracework therethrough.

19. The supportive spinal brace as claimed in claim 18, further comprising the tubular brace work and wherein the tubular brace work comprises at least one of a tubular T-Piece, 90° and parallel offset components.

20. The supportive spinal brace as claimed in claim 19, wherein distal ends of the components comprise apertures for the insertion of a through pin of a circlip connected therethrough.

21. The supportive spinal brace as claimed in claim 1, wherein medial faces of the lateral plates define a vertical channel and wherein anterior surface of the rotatably interlocking components define a widthwise channel.

* * * * *